United States Patent
Glynn et al.

(10) Patent No.: US 9,742,130 B2
(45) Date of Patent: Aug. 22, 2017

(54) LEAD CONNECTOR WITH DISTAL FRAME

(71) Applicant: HERAEUS DEUTSCHLAND GMBH & CO. KG, Hanau (DE)

(72) Inventors: Jeremy Glynn, Buffalo, MN (US); Dan Richter, Hudson, WI (US); LeRoy Calander, Harris, MN (US)

(73) Assignee: Heraeus Deutschland GmbH & Co. KG, Hanau (DE)

( * ) Notice: Subject to any disclaimer, the term of this patent is extended or adjusted under 35 U.S.C. 154(b) by 0 days.

(21) Appl. No.: 14/959,539

(22) Filed: Dec. 4, 2015

(65) Prior Publication Data
US 2016/0087383 A1 Mar. 24, 2016

Related U.S. Application Data

(62) Division of application No. 13/756,017, filed on Jan. 31, 2013, now Pat. No. 9,209,544.

(51) Int. Cl.
*H01R 33/20* (2006.01)
*H01R 24/58* (2011.01)
(Continued)

(52) U.S. Cl.
CPC .......... *H01R 24/58* (2013.01); *A61N 1/0563* (2013.01); *A61N 1/3752* (2013.01);
(Continued)

(58) Field of Classification Search
CPC ........ H01R 24/58; H01R 24/38; H01R 13/04; H01R 2107/00; H01R 2201/12;
(Continued)

(56) References Cited

U.S. PATENT DOCUMENTS 6,817,905 B2    11/2004 Zart et al.
7,083,474 B1    8/2006 Fleck et al.
(Continued)

FOREIGN PATENT DOCUMENTS

WO    0199239    12/2001

OTHER PUBLICATIONS

International Search Report and the Written Opinion for International Application No. PCT/US2014/013569 mailed Mar. 31, 2014 (10 pages).

(Continued)

*Primary Examiner* — Jean F Duverne
(74) *Attorney, Agent, or Firm* — Dicke, Billig & Czaja, PLLC

(57) ABSTRACT

A lead connector for an implantable medical device includes a cylindrical connector body having a proximal end and a distal end. A distal frame forms the distal end and a remainder of the connecter body is a mold material. A plurality of shafts extending through the distal frame from a rear face to a front face, the rear face abutting the mold material forming the remainder of the connector body. A plurality of ring contacts are in the connector body. A plurality of wires are coupled to a ring contact and extend through the mold material and through a corresponding one of the shafts. The mold material forming the remainder of the connector body extends partially into each shaft and about the corresponding conductive wire to form a plug.

13 Claims, 9 Drawing Sheets

(51) Int. Cl.
*H01R 13/04* (2006.01)
*A61N 1/375* (2006.01)
*A61N 1/05* (2006.01)
*H01R 24/38* (2011.01)
*B29C 45/14* (2006.01)
*H01R 107/00* (2006.01)

(52) U.S. Cl.
CPC .. *B29C 45/14065* (2013.01); *B29C 45/14549* (2013.01); *H01R 13/04* (2013.01); *H01R 24/38* (2013.01); *B29C 45/14639* (2013.01); *B29C 2045/14131* (2013.01); *H01R 2107/00* (2013.01); *H01R 2201/12* (2013.01); *Y10T 29/4922* (2015.01)

(58) Field of Classification Search
CPC .......... H01R 13/5224; B29C 45/14549; B29C 45/14065; B29C 45/14639; B29C 2045/14131; A61N 1/0563; A61N 1/3752; Y10T 29/4922
USPC ......................................................... 439/675
See application file for complete search history.

(56) References Cited

U.S. PATENT DOCUMENTS

| | | | |
|---|---|---|---|
| 7,167,749 B2 | 1/2007 | Biggs et al. | |
| 7,175,478 B2 * | 2/2007 | Ollivier | H01R 13/5224 439/669 |
| 7,241,180 B1 * | 7/2007 | Rentas Torres | A61N 1/05 439/668 |
| 7,489,968 B1 | 2/2009 | Alexander et al. | |
| 7,601,033 B2 | 10/2009 | Ries et al. | |
| 7,983,754 B2 | 7/2011 | Kessler et al. | |
| 8,382,529 B2 * | 2/2013 | Lim | A61N 1/3752 439/669 |
| 8,628,348 B2 | 1/2014 | Ries et al. | |
| 8,641,436 B2 * | 2/2014 | Regnier | H01R 24/58 439/218 |
| 8,673,194 B2 | 3/2014 | Lee et al. | |
| 8,761,887 B2 | 6/2014 | Schramm et al. | |
| 8,914,110 B2 | 12/2014 | He et al. | |
| 9,072,909 B1 * | 7/2015 | Hughes | A61N 1/3752 |
| 9,101,776 B2 * | 8/2015 | Hughes | A61N 1/3752 |
| 9,209,544 B2 | 12/2015 | Glynn et al. | |
| 2008/0303728 A1 | 12/2008 | Lee et al. | |
| 2010/0210146 A1 * | 8/2010 | Jang | B29C 45/0055 439/638 |
| 2012/0151765 A1 | 6/2012 | James, IV et al. | |
| 2014/0213118 A1 | 7/2014 | Glynn et al. | |

OTHER PUBLICATIONS

Restriction Requirement for U.S. Appl. No. 13/756,017 mailed Sep. 4, 2014 (16 pages).
Restriction Requirement for U.S. Appl. No. 13/756,017 mailed Nov. 10, 2014 (7 pages).
Office Action for U.S. Appl. No. 13/756,017 mailed Feb. 26, 2015 (10 pages).
Notice of Allowance for U.S. Appl. No. 13/756,017 mailed Aug. 3, 2015 (8 pages).

* cited by examiner

LEAD CONNECTOR WITH DISTAL FRAME

CROSS-REFERENCE TO RELATED APPLICATIONS

This application is a divisional of U.S. patent application Ser. No. 13/756,017, entitled "LEAD CONNECTOR WITH DISTAL FRAME AND METHOD OF MANUFACTURE," having a filing date of Jan. 31, 2013, which is incorporated herein by reference.

BACKGROUND

An implantable medical lead typically includes a tubular-shaped main lead having one or more conductors or coils to sense or provide stimulative biologic, electrical signals, and a lead connector coupled to one end of the main lead. The lead connector is, in-turn, configured to electrically and mechanically plug into and couple to a header or connector bore of a pacemaker, implantable cardioverter defibrillator ("ICD"), or other type of pulse generator.

An IS4/DF4 lead connector is standardized lead connector having an injection molded, reaction injection molded (RIM) or potted, cylindrical body (typically of a thermoplastic, or thermoset material), the connector body having a proximal end configured to connect into a header of an active implantable device of some type, and a distal end configured to connect to the conductors/coils within the main lead. Such lead connectors have multiple electrical contacts in the form of contact rings which are spaced along and are flush with a surface of the connector body. Lead connectors may also include a pin contact extending from the proximal end. A conductor typically extends through the lead body from each contact ring and projects from the distal end of the molded body so as to provide a connection point for the conductors of the main lead. Similarly, a main body pin may extend along a central axis of the lead connector from the pin contact at the proximal end and also project from the distal end of the molded body.

Conventional practices for the manufacture of lead connectors include an injection molding process, or a reaction injection molding process, or liquid silicone molding process, or a potting process wherein the ring connectors, conductive pins, and the central pin/pin contact (if being employed) are arranged within a mold cavity. A thermoplastic material, or other suitable material, is then injected into the mold cavity to over-mold the conductive pins, ring connectors, and main body pin to form the cylindrical body of the lead connector.

Tight tolerances are required for the safe and effective performance of lead connectors, including IS4/DF4 connectors. However, the injection molding process presents many challenges and shortcomings that make maintenance of such tight tolerance difficult to meet and which can result in high production costs and low manufacturing yields.

BRIEF DESCRIPTION OF THE DRAWINGS

The accompanying drawings are included to provide a further understanding of embodiments and are incorporated in and constitute a part of this specification. The drawings illustrate embodiments and together with the description serve to explain principles of embodiments. Other embodiments and many of the intended advantages of embodiments will be readily appreciated as they become better understood by reference to the following detailed description. The elements of the drawings are not necessarily to scale relative to each other. Like reference numerals designate corresponding similar parts.

DETAILED DESCRIPTION

Figure 1:
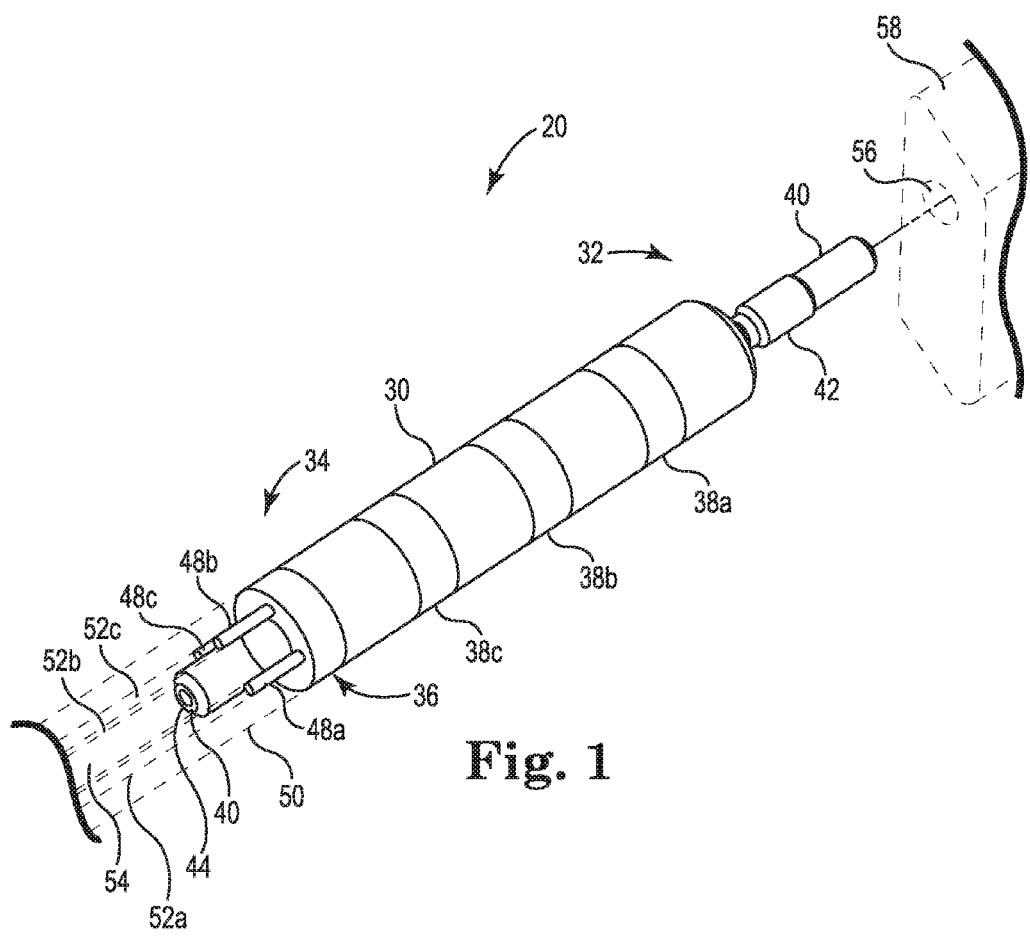
FIG. 1 is a perspective view of a lead connector according to one embodiment.

In the following Detailed Description, reference is made to the accompanying drawings, which form a part hereof, and in which is shown by way of illustration specific embodiments in which the invention may be practiced. In this regard, directional terminology, such as "top," "bottom," "front," "back," "leading," "trailing," etc., is used with reference to the orientation of the Figure(s) being described. Because components of embodiments can be positioned in a number of different orientations, the directional terminology is used for purposes of illustration and is in no way limiting. It is to be understood that other embodiments may be utilized and structural or logical changes may be made without departing from the scope of the present invention. The following detailed description, therefore, is not to be taken in a limiting sense, and the scope of the present invention is defined by the appended claims.

It is to be understood that the features of the various exemplary embodiments described herein may be combined with each other, unless specifically noted otherwise.

In one embodiment, a method of manufacturing a lead connector for an implantable medical device includes connecting proximal ends of a plurality of conductive wires to an inner surface of a corresponding ring contact. A distal frame is placed over distal ends of each of conducive wires of the plurality of conductive wires, the distal ends pass through corresponding shafts in the distal frame from a rear face of the distal frame and extend beyond a front face of the distal frame. The distal frame is arranging along with the conductive wires and corresponding ring contacts within a mold cavity and the mold cavity is filled with a mold material, the mold material abutting the rear face of the distal frame. The resulting lead connector is removed from the mold cavity.

In one embodiment, the method using a separately formed distal frame provides several advantages over known processes. The distal frame securely positions the conductive wires more accurately within the mold cavity. As such, there is less movement of the wires during the assembly and molding process, thereby reducing the occurrence of shorts. Use of the distal frame also simplifies the mold tool by simplifying and reducing the exit holes required. The distal frame also provides a simplified process for aligning and positioning the conductive wire within the mold cavity saving assembly time.

In one embodiment, the method includes reflowing a material of the distal frame along the rear face with the mold material filling the mold cavity so that the material of the distal frame along the rear face joins with the mold material filling the mold cavity. This forms a contiguous body of the resulting lead connector.

In one embodiment, the method includes using a mold material to fill the mold cavity that is same as a material of the distal frame, making the resulting lead connector a uniform material.

In one embodiment, the method includes employing a distal frame with shafts having an inner diameter larger than an outer diameter of a corresponding conductive wire passing through the shaft. A portion of a length of each shaft is filled about a circumference of the corresponding conductive wire with the mold material during the filling of the mold cavity. This forms a plug within the shaft about the conductive wire. This prevents mold material from extending beyond the distal frame thereby negating need for any post-processing of the lead connector to remove excess or flash mold material.

In one embodiment, the method includes arranging a central pin along a central axis through the ring contacts, the central pin extending within a corresponding central lumen of the distal frame. In one embodiment, placing the distal frame over the distal ends of each of the plurality of conductive wires reduces shorting between conductive wires as the mold material fills the mold cavity.

In one embodiment, each conductive wire and the corresponding ring contact to which the proximal end of the conductive wire is connected form a subassembly. Prior to placing the distal frame over distal ends of the conductive wires, the subassemblies are arranged such that conductive wires of a portion of the subassemblies passes through ring contacts of one or more other subassemblies.

In one embodiment, a lead connector for an implantable medical device includes a cylindrical connector body having a proximal end and a distal end, a distal frame forming the distal end and a remainder of the connecter body comprising a mold material, a plurality of shafts extending through the distal frame from a rear face to a front face, the rear face abutting the mold material forming the remainder of the connector body. A plurality of ring contacts spaced apart along a length of the connector body between the proximal end and the distal end. A plurality of wires, each wire each wire having a proximal end coupled to an internal surface of a corresponding ring contact and extending through the mold material and through a corresponding one of the shafts and beyond the front face of the distal frame to a distal end of the wire. Mold material forming the remainder of the connector body extends partially into each shaft and about the corresponding conductive wire to form a plug.

In one embodiment, such a lead connector has several advantages. The distal frame securely positions the conductive wires more accurately within the mold cavity. Use of the distal frame also simplifies the mold tool by simplifying and reducing the exit holes required. The distal frame also provides a simplified process for aligning and positioning the conductive wire within the mold cavity saving assembly time. The distal frame also prevents flashing negating need for post-processing.

In one embodiment of the lead connector, an inner diameter of each shaft through the distal frame is larger than an outer diameter of the corresponding wire passing through the shaft. In one embodiment, a material of the distal frame is different from the mold material forming the remainder of the connector body. In one embodiment, the distal frame includes a plurality of lead-in structures extending from the rear face, one corresponding to each shaft, configured to receive and guide a corresponding wire into the corresponding shaft.

In one embodiment, a method of manufacturing a lead connector for an implantable medical device includes forming a distal frame having a plurality of through-holes extending from a rear face to a front face in a first process. First ends of each of a plurality of conductive pins are connected to an inner surface of a corresponding ring connector. The conductive pins and corresponding ring connectors are arranging into a desired configuration. The distal frame is placed the over second ends of each of the conductive pins such that each of the conductive pins passes through a corresponding one of the through-holes with the second extend extending beyond the front face of the distal frame. The mold cavity is filled with a mold material in a second process to overmold the connector assembly, the mold material abutting the rear face of the distal frame. The resulting lead connector is removed from the mold cavity, distal forming a distal geometry of the lead connector.

In one embodiment, the method provides several of the advantages discussed above, including the distal frame securely positioning the conductive wires, reducing the occurrence of shorts, simplifying the mold tool, and saving assembly and post-processing time.

In one embodiment of the method, the first process comprises a machining process or a molding process. In one embodiment, the distal frame is formed by the first process including forming the distal frame with a material that is different from the mold material of the second process. In one embodiment, the second process includes reflowing a material of the distal frame at an interface region along the rear face so that the material of the distal frame at the rear surface joins with the mold material of the second process. This forms a contiguous body of the resulting lead connector.

In one embodiment, forming the distal frame includes forming the through-holes with an inside diameter is greater than an outside diameter of the conductive pins. The second process includes flowing the mold material into a portion of a length of each through-hole to form a plug around each conductive pin. This prevents flashing of the mold material.

In one embodiment, forming the distal frame includes forming the through-holes with tapered openings or lead-in structures on the rear face. These can further aid in directing mold material and stabilizing conductive wires.

In one embodiment, the distal frame is formed with an outside diameter at the rear face that is equal to an inside diameter of the mold cavity. As such, the distal frame can block mold material from flowing past the distal frame.

In one embodiment, a distal frame for a lead connector includes a base having a front face, a rear face and an outer diameter, the base configured with a plurality of shafts extending between the front face and the rear face. The distal frame includes an extension extending from the front face of the base and configured with a central lumen extending through the extension. The plurality of shafts are configured to receive a plurality of wires from the lead connector such that the wires extend through the rear face of the base and extend out beyond the front face of the base. A cylindrical connector body of the lead connector is configured adjacent the rear face of the base and configured to at least partially extend into the plurality of shafts in the base.

In one embodiment, the distal frame provides several of the advantages discussed above, including securely positioning the conductive wires, reducing the occurrence of shorts, simplifying the mold tool, and saving assembly and post-processing time.

In one embodiment, the connecter body comprises a mold material configured to flow against the rear face of the distal frame thereby causing the distal frame to reflow at its rear face thereby forming a reflow interface. This effectively couples the connector body and the distal frame.

In one embodiment, the outer diameter of the distal frame is configured to match an inside diameter of a mold cavity. As such, during molding of the connector body the rear face of the base is configured to block the flow of mold material thereby preventing the mold material from reaching the front face of the base. This negates any need for post-processing flash material.

In one embodiment, the distal frame includes tapered openings or lead-in structures at the through-holes on the rear face. These can further aid in directing mold material and stabilizing conductive wires.

Figure 2:
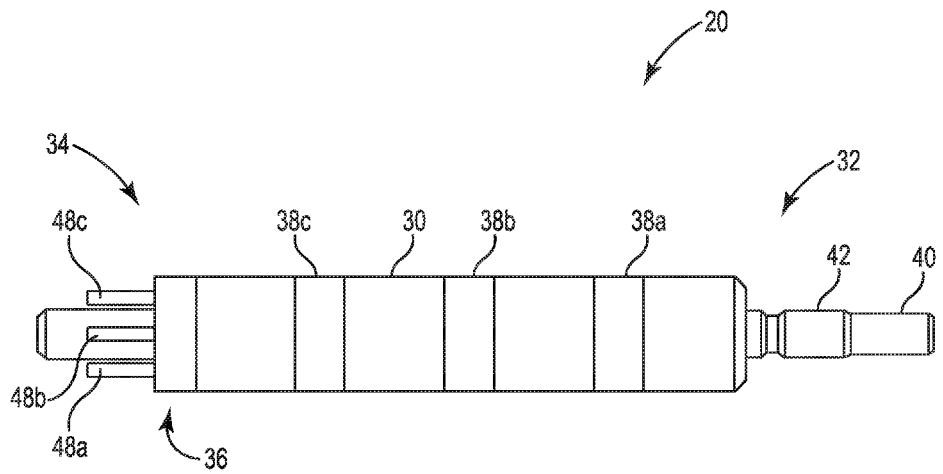
FIG. 2 is a side view of the lead connector depicted in FIG. 1, according to one embodiment.

FIG. 1 is a perspective view, and FIG. 2 is a side view of an example of a lead connector 20 for an implantable medical device, such as an IS4/DF4 lead connector. Lead connector 20 includes a cylindrical body 30 having a proximal end 32 and a distal end 34 formed by a distal frame 36, according to one embodiment. As will be described in greater detail herein, distal frame 36 is a separately formed component which positions and secures components of lead connector 20 during manufacture, and which itself becomes integral with and defines the geometry of distal end 34 of body 30.

Lead connector 20 further includes ring contacts 38a, 38b, 38c, disposed in a spaced-apart fashion along a longitudinal length of body 30, and a central pin 40 axially extending from proximal end 32 having a pin contact 42. Ring contacts 38a-38c are imbedded in and have a same outer diameter as body 30 so as to provide cylindrical body 30 with a uniform circumferential surface. Body 30 may be formed of an electrically non-conductive polymer material (e.g. polyurethane, polyetheretherketone (PEEK), polysulfone, etc.), epoxy, liquid silicone rubber, or any other suitable type of electrically non-conductive material, with distal frame 36 being formed of a same or different material from that of body 30.

Conductive pins 48a, 48b, and 48c axially extend through body 30 from ring contacts 38a-38c and project from distal end 34 of body 30. According to one embodiment, conductive pins 48a-48c are generally rigid wires that form conductive pins 48a-48c. Similarly, central pin 40 extends axially through body 30 and projects from distal end 34, with central pin 40 defining a central lumen 44. Conductive p 48a-48c serve as a contact point to which conductors 52a, 52b, and 52c of a flexible implantable lead 50 (dashed lines in FIG. 1) are electrically and mechanically connected, such as by laser welding, for example, to thereby place lead conductors 52a-52c in electrical communication with ring contacts 38a-38c. Lead 50 may also include a central conductor 54 which is in electrical communication with pin contact 42 via central lumen 44. Conductors 52a-52c and central conductor 54 extend through lead 50 to corresponding coil or sensor.

Lead connector 20 is configured to be inserted into a receptacle or bore of 56 of header of a pulse generator 58 of some type, such as a pacemaker or implantable cardioverter defibrillator ("ICD"), for example. Complementary contacts within pulse generator contacts ring contacts 38a-38c and pin contact 42, thereby placing pulse generator 58 in electrical communication with sensors and/or coils associated with lead 50.

It is noted that while lead connector 20 is described primarily in the context of an IS4/DF4 lead connector, the use of distal frame 36 and manufacturing techniques described herein are applicable to other types of lead connectors as well. Accordingly, the features of lead connector 20, including distal frame 36, and methods of manufacture described herein should not be interpreted as being limited to only IS4/DF4 lead connectors.

As described earlier, conventional techniques for the manufacture of lead connectors include an injection molding process, reaction injection molding process, silicone molding process, or potting process. After joining the conductive pins to the contact rings to form subassemblies (typically there are three subassemblies, one for each contact ring/conductive pin), the subassemblies, along the central pin/pin contact if being employed, are loaded into a mold cavity. The conductive pins and central pin/pin contact are positioned within the mold cavity with their ends extending through corresponding exit holes formed in the mold tool steel. A thermoplastic material, or other suitable material, is then injected under into the cavity to over-mold the subassemblies and main contact pin to form the cylindrical body of the lead connector.

Tight tolerances are required for the safe and effective performance of lead connectors, including IS4/DF4 connectors. Such tight tolerances can result in high production costs and low manufacturing yields. While conventional techniques for the manufacture of lead connectors are adequate, several shortcomings exist than can adversely impact lead production. First, the high injection pressure used in the injection molding process can cause the conductive pins and central pin to move within the mold cavity, thereby causing the electrical characteristics to potentially vary between lead connectors, and even causing shorting issues should the conductive pins be moved into contact with one another or other conductive elements within the lead connector.

Also, due to normal tolerances in the diameters of the conductive pins and central pin, the exit holes in the mold tool steel may be oversized and allow the thermoplastic material to flash out. Such flash can adversely impact downstream assembly when attaching the main lead to the lead connector and, as such, must be removed by secondary processing. Additionally, it is difficult and time consuming to properly position the subassemblies within the mold cavity and to thread the conductive pins through the corresponding exit holes in the mold steel. Furthermore, separate molds, or at least separate mold components, must be manufactured and employed for each type of lead connector configuration (e.g. 3-pin lead connector with central pin, 3-pin connector without central pin, 4-pin lead connector with central pin, etc.).

According to embodiments described herein, lead connector 20, and methods of manufacture thereof, employ distal frame 36 to address these shortcomings. As will be described in greater detail below, distal frame 36 is manufactured in a first process, and is subsequently used to secure and position conductive pins 48a-48c and central pin 40 (if employed) within a mold cavity. During high pressure injection of mold material (e.g., a thermoplastic, epoxy) into the mold cavity, distal frame 36 holds conductive pins 48a-48c and central pin 40 securely in their desired positions and joins with a remainder of mold material forming body 30. After removal from the mold cavity, distal frame 36 is integral with body 30 and forms the distal geometry of distal end 34 of the finished lead connector 20.

Figure 3:
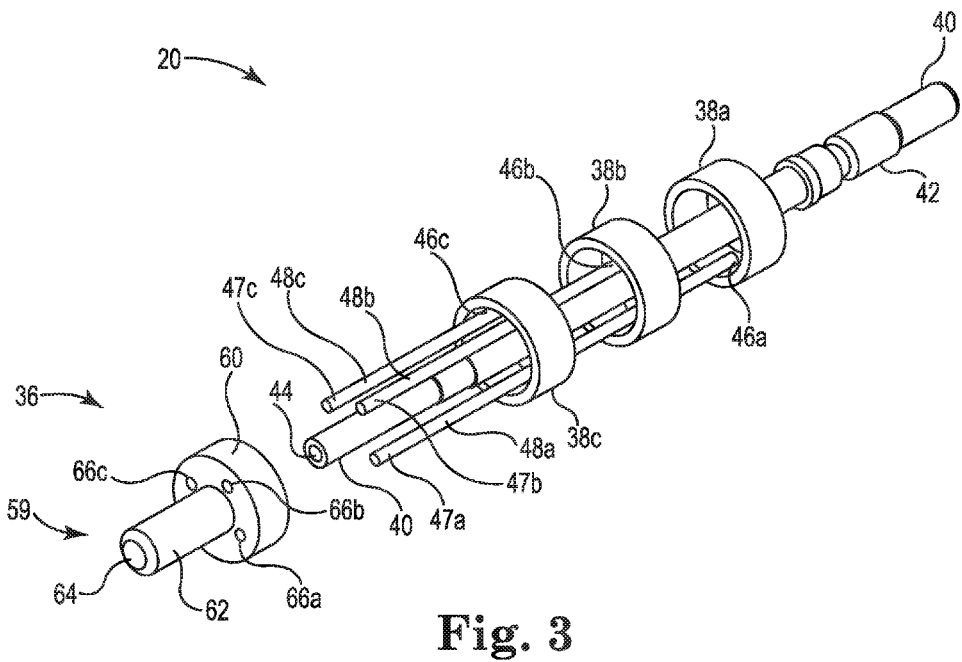
FIG. 3 is a perspective view illustrating portions of a lead connector in a stage of assembly prior to over-molding, according to one embodiment.
Figure 4:
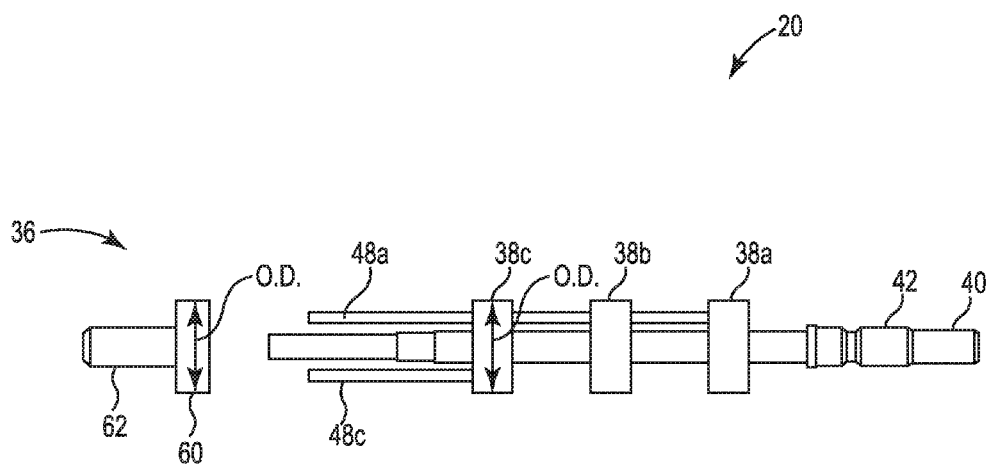
FIG. 4 is a side view of illustrating portion of the lead connector depicted in FIG. 3, according to one embodiment.

FIG. 3 is a perspective view, and FIG. 4 is a side view, illustrating portions of lead connector 20, according to one embodiment, prior to being over-molded to form body 30. As illustrated, prior to the molding process for forming body 30, conductive pins 48a, 48b, and 48c are respectively connected to an inner surface of their corresponding ring contact 38a, 38b, 38c, such as by laser welding, or soldering, for example, to form what are referred to as sub-assemblies, or contact sub-assemblies. Each of conductive pins 48a, 48b, and 48c respectively have proximal ends 46a, 46b, and 46c and distal ends 47a, 47b, and 47b. The contact sub-assemblies are then arranged relative to one another such that conductive pin 48a extends from ring contact 38a through ring contacts 38b and 38c, and conductive pin 48b extends through ring contact 38c toward what will become the distal end 34 of the completed lead connector 20 (as shown in FIGS. 1 and 2). Central pin 40 is also arranged so as to extend through all three ring contacts 38a-38c from what will become proximal end 32 of completed lead connector 20 to what will become the distal end 34.

Figure 5:
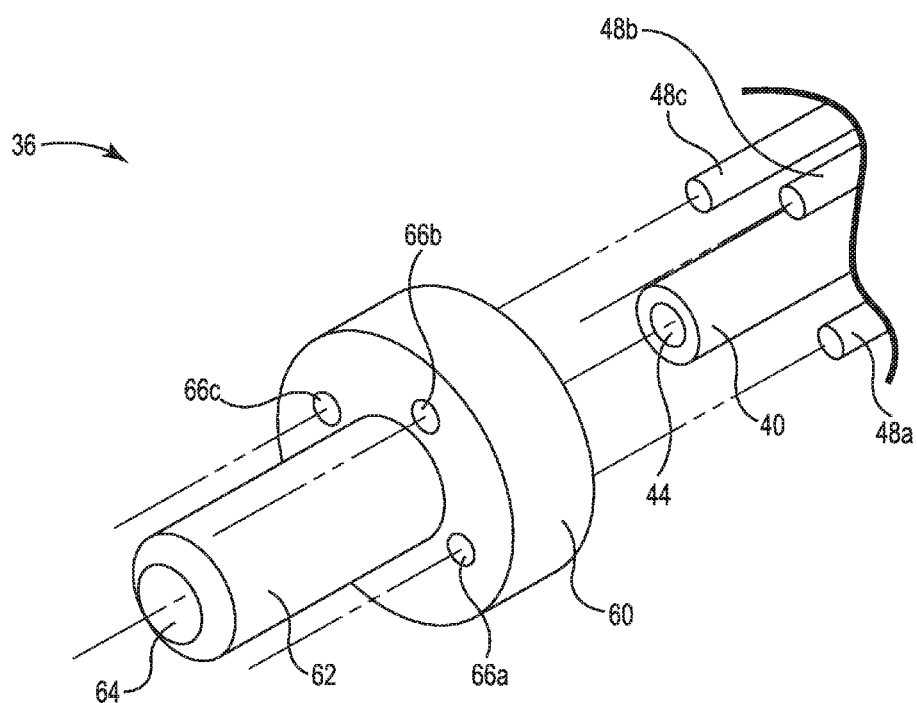
FIG. 5 is a perspective view of a distal frame, according to one embodiment.

According to the illustrated embodiment, distal frame 36 has a stepped cylindrical shape including a cylindrical base 60 having an outer diameter which is equal to the outer diameter (O.D.) of ring contacts 38a-38c, and thus the O.D. of body 30. Distal frame 36 further includes a cylindrical extension 62 having a smaller O.D. than base 60 and extending from base 60 along a central axis thereof, with extension 62 defining a central lumen 64 configured to receive central pin 40. Base 60 includes shafts 66a, 66b, and 66c extending there through from a rear face of base 60 to a front face of base 60 in a pattern such that shafts 66a, 66b, and 66c are respectively configured to align with and receive conductive pins 48a, 48b, and 48c. FIG. 5 is an enlarged view of distal frame 36 illustrating the alignment between central pin 40 and conductive pins 48a-48c with central lumen 64 and shafts 66a-66c.

Figure 6A:
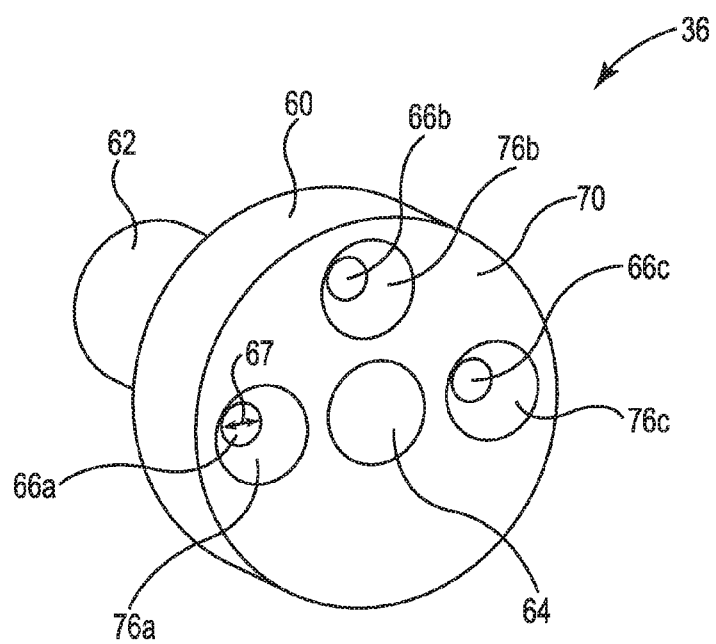
FIG. 6A is a perspective view of a distal frame, according to one embodiment.

FIG. 6A is a perspective view illustrating a rear face 70 of distal frame 36. According to one embodiment, as illustrated, rear face 70 is substantially planar. Each of the shafts 66a-66c has an inside diameter 67. According to one embodiment, rear face 70 includes counter-sunk or tapered openings 76a, 76b, 76c for each of the shafts 66a-66c, wherein each of the tapered openings 76a-76c has an initial diameter larger than inside diameter 67 and which is tapered to match the inside diameter 67. Tapered openings 76a-76c are configured to guide conductive pins 48a-48c into shafts 66a-66c when distal frame is slid onto the distal ends of conductive pins 48a-48c (see FIG. 7).

According to one embodiment, inside diameters 67 of shafts 66a-66c are sized so as to be equal to a nominal outside diameter of conductive pins 48a-48c plus at least a maximum of an allowed tolerance range in the nominal diameter of conductive pins 48a-48c. According to one embodiment, inside diameters 67 are sized to be incrementally larger than the maximum allowed diameter of conductive pins 48a-48c (i.e., incrementally larger than the sum of the nominal diameter plus the maximum allowed tolerance). As will be described in greater detail below (see FIG. 10),
according to one embodiment, tapered openings 76a-76c are configured to direct a flow of thermoplastic, (or other selected material) about conductive pins 48a-48c and into a portion of shafts 66a-66c to about conductive pins 48a-48c so as to from a plug or seal thereabout within shafts 66a-66c (see FIG. 10).

Distal frame 36 is formed in a process separate from that of the over-molding process which forms a remainder of body 30 and over-molds conductive pins ring contacts 38a-38c, central pin 40, and conductive pins 48a-48c. According to one embodiment, distal frame 36 is formed in a separate injection molding process. According to one embodiment, distal frame 36 is formed by a machining process. According to one embodiment, distal frame 36 is formed with a same mold material employed to form a remainder of body 30. According to one embodiment, distal frame 36 is formed with a mold material different from that employed to form a remainder of body 30.

Figure 6B:
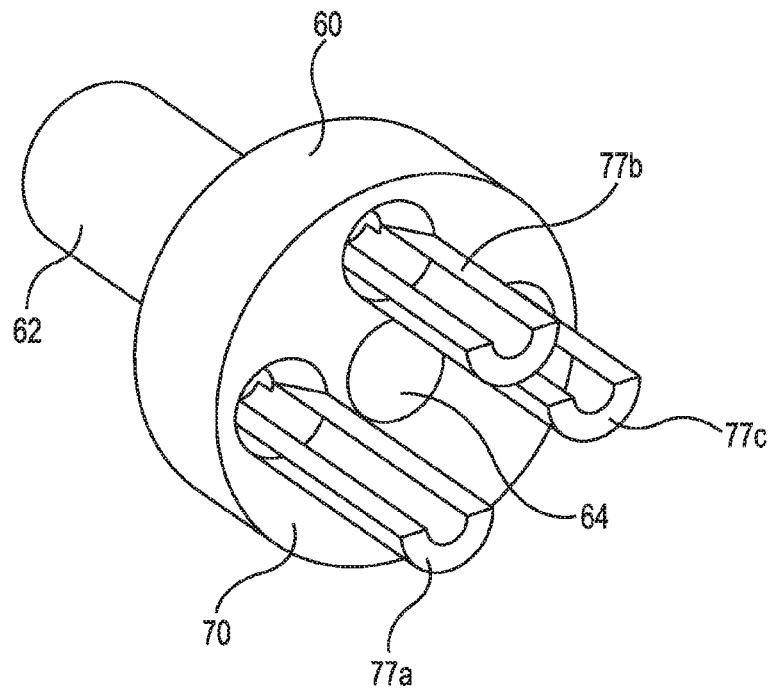
FIG. 6B is a perspective view of a distal frame, according to one embodiment.

FIG. 6B is a perspective view illustrating rear face 70 of distal frame 36, according to one embodiment. As illustrated by FIG. 6B, in lieu of tapered openings, distal frame 36 includes a lead-in structure 77a, 77b, 77c for each of the shafts 66a-66c. According to one embodiment, as illustrated, lead-in structures 77a-77c is a partial tube forming a trough-like structure that extends from rear surface 70 and is configured to support and guide the conductive pins 48a-48c into the corresponding shafts 66a-66c. In addition to providing support to conductive pins 48a-48c, lead-in structures 77a-77c provide additional surface area which, as described in greater detail below, can reflow during a molding process to form a remainder of body 30, and thereby provide greater adhesion/bonding between distal frame 36 and the remainder of body 30 of lead connector 20. It is noted that lead-in structures may have other forms as well. For example, according to one embodiment (not illustrated), lead-in structures 77a-77c comprise tubes through which conductive pins 48a-48c slide, in lieu of partial tubes as illustrated by FIG. 6B.

Figure 7:
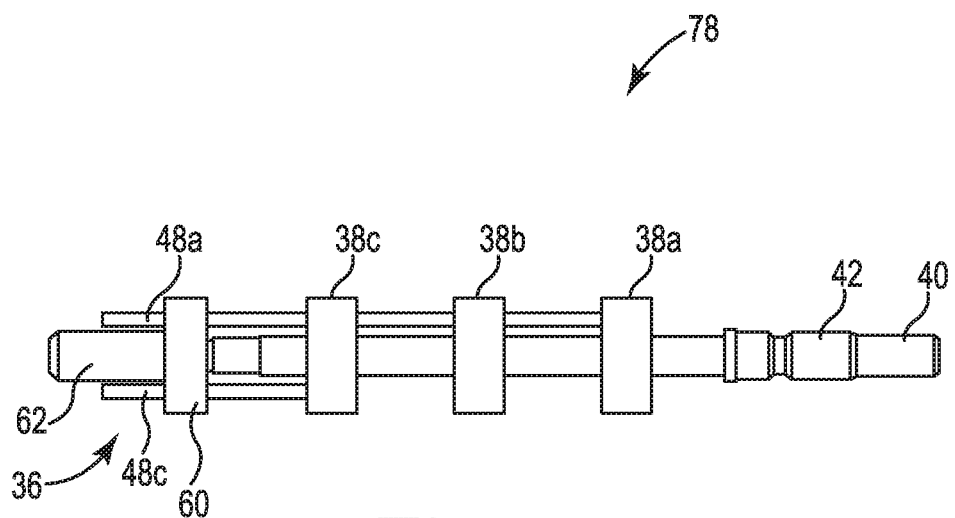
FIG. 7 is a side view illustrating a connector assembly prior to over-molding, according to one embodiment.

FIG. 7 is a side view illustrating a connector assembly 78 prior to over-molding, according to one embodiment. After arranging the contact sub-assemblies and central pin 40 such that conductive pin 48a extends from ring contact 38a through ring contacts 38b and 38c, conductive pin 48b extends through ring contact 38c, and central pin 40 extends through all three ring contacts 38a-38c (see FIGS. 3 and 4), distal frame 36 is positioned over (e.g. slid onto) the distal ends of conductive pins 38a-38c and central pin 40 to form connector assembly 78. Connector assembly 78 includes conductive pins 48a-48c extending through shafts 66a-66c in base 60 (such that conductive pins 48a-48c extend out from a front face of distal frame 36), and central pin 40 extending within central lumen 64 of cylindrical extension 62 of distal frame 36. Connector assembly 78 is then placed into a mold for over-molding to produce a completed lead connector 20, as illustrated by FIGS. 1 and 2.

Figure 8:
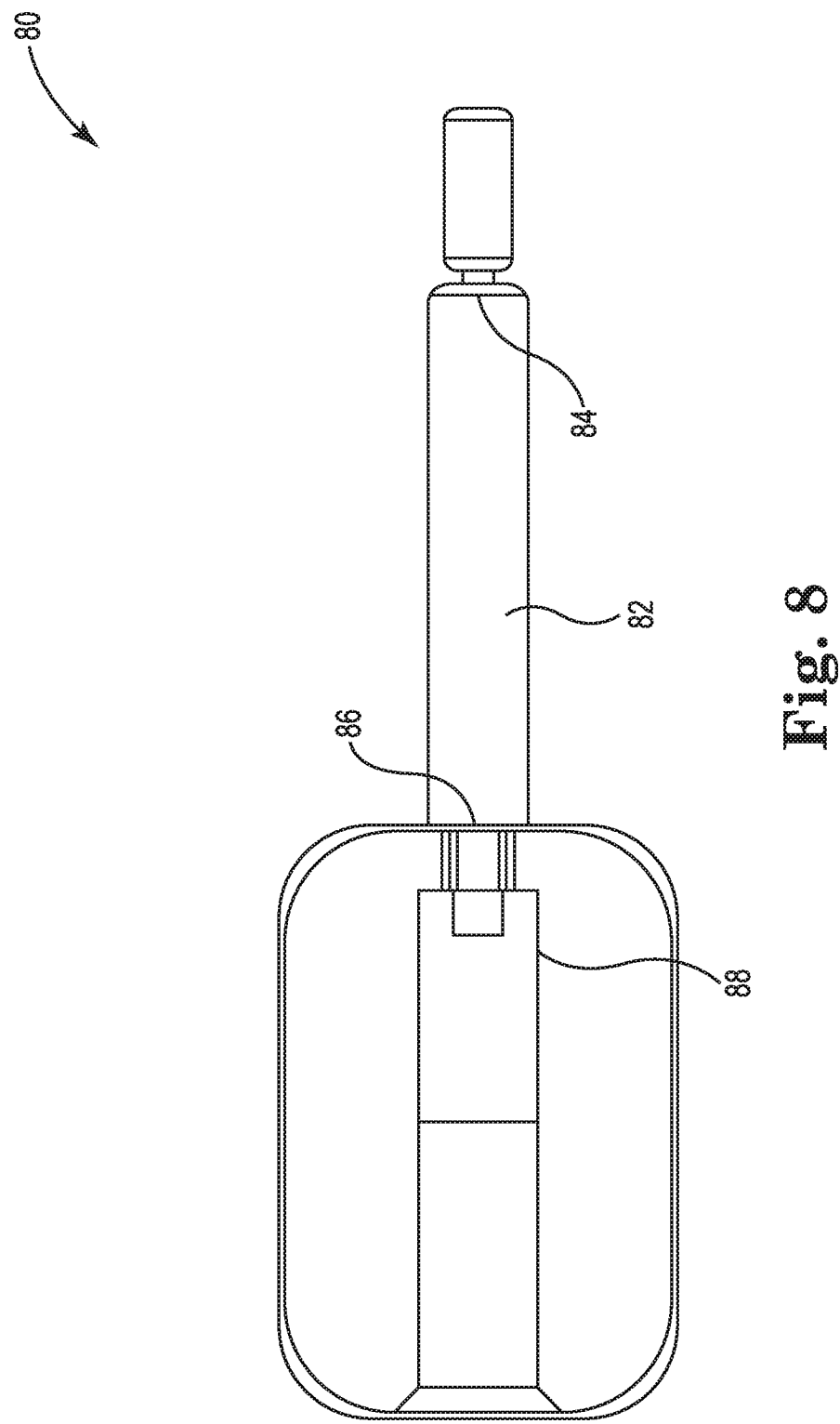
FIG. 8 illustrates a mold for over-molding a connector assembly as depicted in FIG. 7, according to one embodiment.

FIG. 8 generally illustrates portions of an injection molding system 80 for over-molding connector assembly 80 to form body 30 and, thereby, form completed lead connector 20. Molding system 80 includes a mold cavity 82 configured to receive a connector assembly, such as connector assembly 78. According to one embodiment, mold cavity 82 is substantially tubular or cylindrical in shape, and has an inside diameter equal to that of the outside diameter of body 30 of lead connector 20. Mold cavity 82 includes an opening 84 at one end through which the proximal end of central pin 40, including pin contact 42, extends. Mold cavity 86 includes an opening 86 at an opposing end through which portions of a front face of distal frame 36 extend, including the portions of conductive pins 38a-38c extending through base 60 and cylindrical extension 62 and a length of central pin 40 therein. Mold system 80 further includes a block 88 configured to retain a portion of cylindrical extension 62 of distal frame 36 and which acts as a stop for conductive pins 38a-38c extending through base 60.

Figure 9:
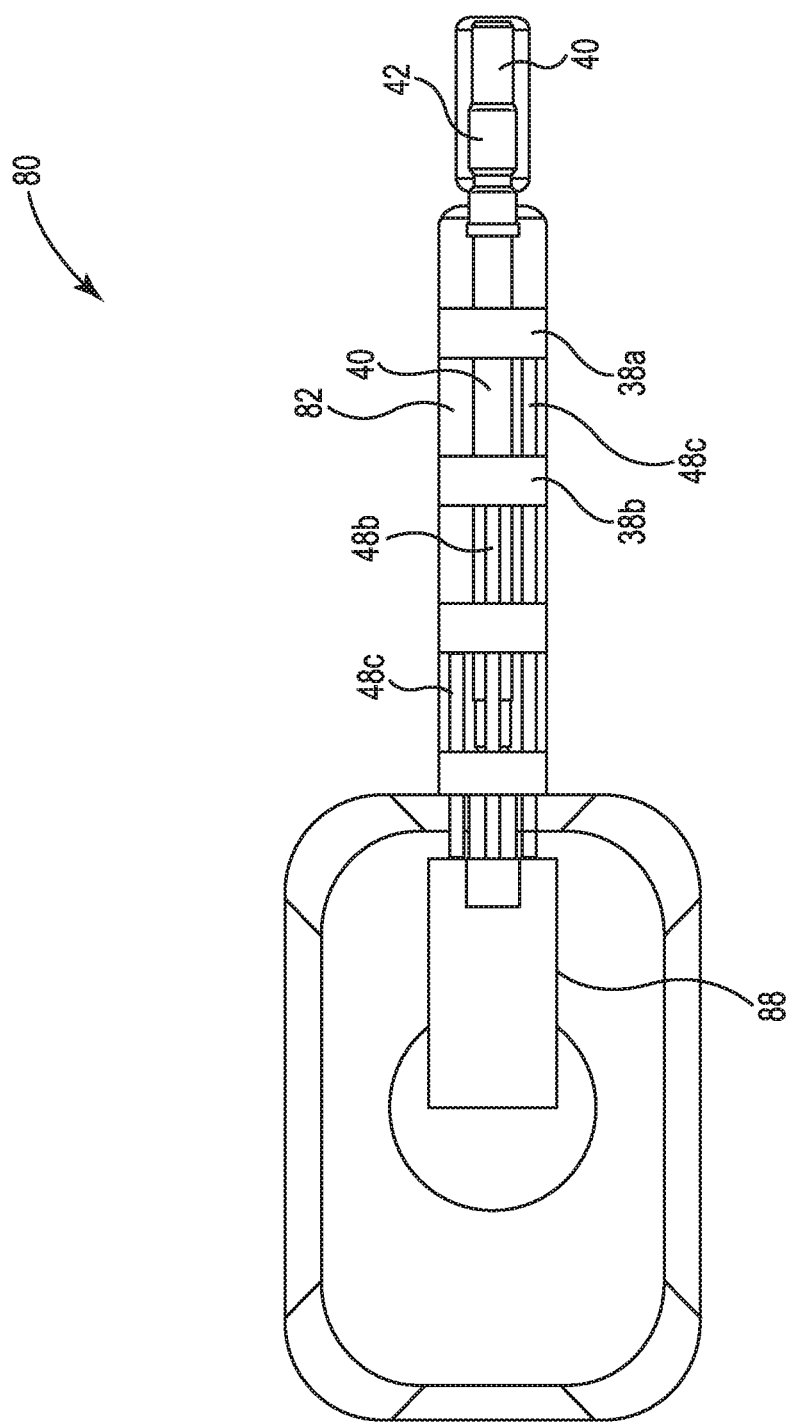
FIG. 9 illustrates a connector assembly loaded in the mold depicted in FIG. 9, according to one embodiment.

FIG. 9 illustrates the mold system 80 of FIG. 7 with connector assembly 78 loaded into mold cavity 82. As illustrated, central pin 40, including pin contact 42, extends through mold cavity opening 84. Similarly, portions of a front face of distal frame 36, including the portions of conductive pins 38a-38c extending through base 60, and cylindrical extension 62 and a length of central pin 40 therein, extend through mold cavity opening 84. After connector assembly 78 is loaded into mold cavity 82, mold material is injected into mold cavity 82 to over-mold those portions of connector assembly 78 within mold cavity 82 and form connector body 30. The resulting finished lead connector 20 (as illustrated by FIGS. 1 and 2) is then removed from mold system 80.

Figure 10:
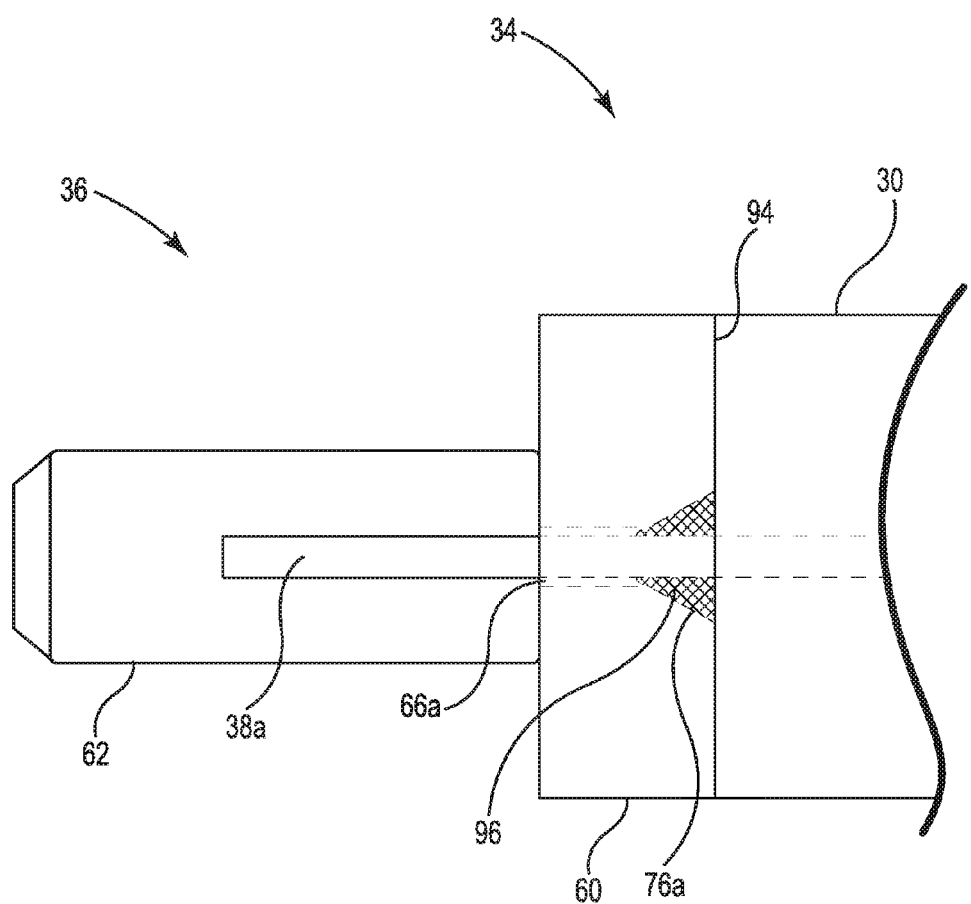
FIG. 10 is a sectional view of portions of a lead connector after molding.

FIG. 10 is a cross-sectional view illustrating portions the distal end 34 of lead connector 20, including portions of distal frame 36. During the molding process, the mold material injected into mold cavity 82 abuts rear face 70, and a portion of the material of distal frame 36 on rear face 70 reflows and joins with the mold material injected into mold cavity 82 to form part of body 30. By the joining of the material of rear face 70 with the material injected into mold cavity 82, distal frame 36 merges with and becomes an integral part of body 32, forming the geometry of distal end 34 thereof. This reflow interface or zone between the rear face 70 and a remainder of the body 30 is indicated by a reflow line 94. As mentioned above, the material of distal frame 36 may be the same as, or may be different from, the material injected into mold cavity 82 during the injection molding process to form a remainder of body 30.

According to one embodiment, as illustrated, an amount of injected molded material 96 (represented by the cross-hatched area in FIG. 10) flows into the tapered openings 76a-76c of shafts 66a-66c on the rear face of distal frame 36 (note that only tapered opening 76a, shaft 66a, and conductive pin 38a are illustrated in FIG. 10). The mold material flows in tapered opening 76a and at least partially into shaft 66a about conductive pin 38a before cooling and forming a plug about conductive pin 38a that seals body 38. By forming distal frame 36 with shafts 66a-66c having lengths sufficient to result in the inject mold material cooling before reaching the ends thereof, distal frame 36 eliminates the "flashing" of mold material from the shafts 66a-66c and, thereby, eliminates the need for secondary processing to remove such flashed material.

Figure 11:
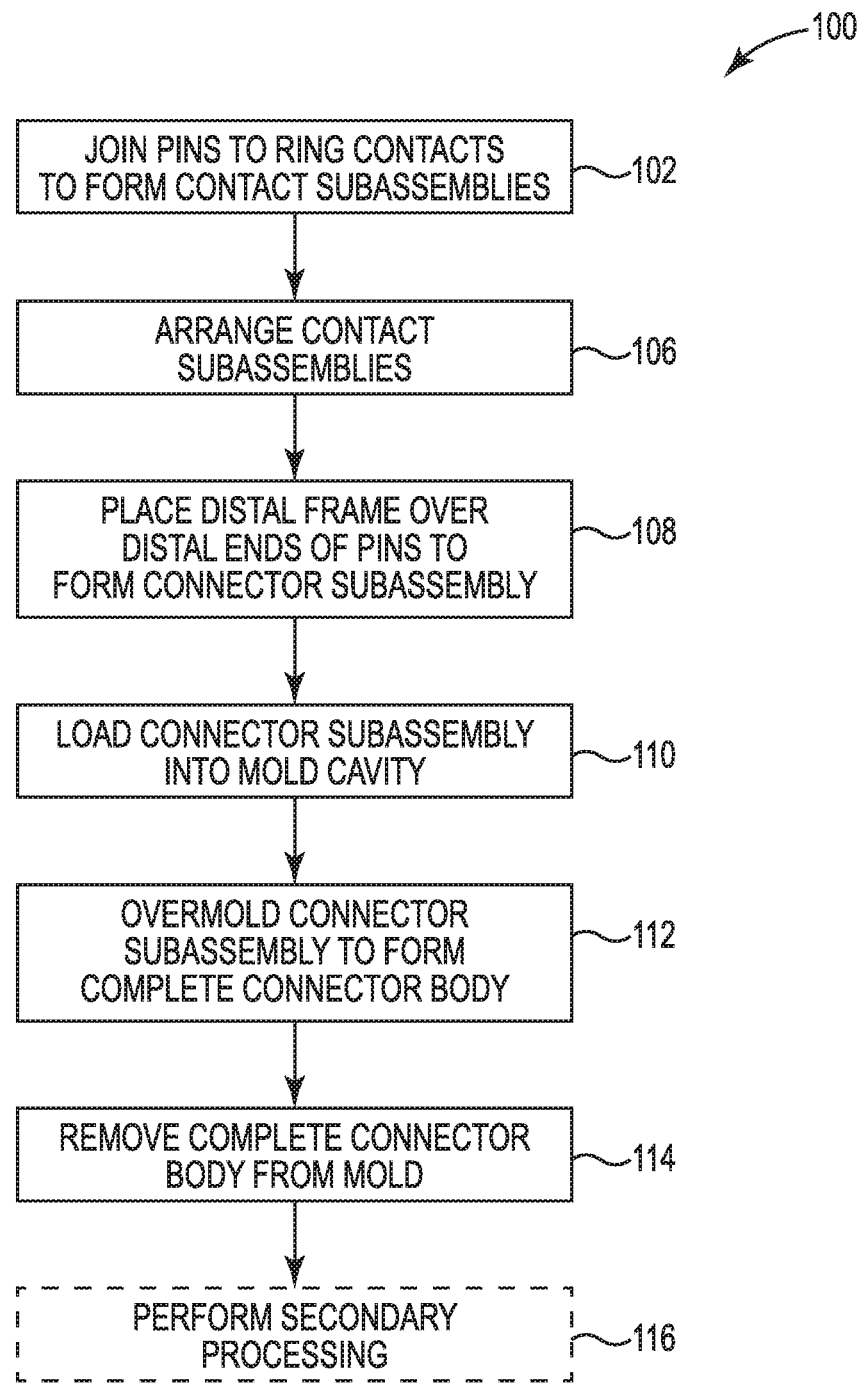
FIG. 11 is flow diagram illustrating a process for forming a lead connector, according to one embodiment.

FIG. 11 is flow diagram illustrating a process 100 for forming a lead connector, such as lead connector 20, according to one embodiment. Process 100 begins at 102 where conductive pins, such as conductive pins 48a-48c are joined (e.g. by laser welding) to ring contacts, such as ring contacts 38a-38c, to form contact sub-assemblies.

At 106, the contact sub-assemblies are arranged into a desired configuration. For example, according to one embodiment, as illustrated by FIGS. 3 and 4, conductive pin 48a extends from ring contact 38a through ring contacts 38b and 38c, conductive pin 48b extends through ring contact 38c, and central pin 40 extends through all three ring contacts 38a-38. At 108, distal frame is installed over the distal ends of conductive pins 38a-38c and central pin 40 to form a connector assembly, such as connector assembly 78 (see FIG. 7).

At 110, the connector assembly, such as connector assembly 78, is loaded into a mold cavity of an injection molding system, such as mold cavity 82 of molding system 80 (see FIGS. 8 and 9). Mold material is injected into the mold cavity to over-mold the portions of connector assembly 78 within the mold cavity 82. At 114, the finished lead connector, such as lead connector 20, is removed from the mold. At 116, if required, post mold secondary processing is performed, such as annealing, plasma treatment, machining, trimming or cleaning. For example, some thermoplastics require annealing in order to meet dimensional specification. Machining can be done to add a feature on an inner diameter or outer diameter of the lead connector that cannot be effectively formed via injection molding.

Employing a separately formed, or pre-formed distal frame 36, as described herein, in the formation of a lead connector, such as, lead connector 20, provides several advantages over known processes. First, distal frame 36 positions the conductive pins/wires, such as conductive pins 48a-48c, more securely and accurately within the mold cavity, such as mold cavity 82, so that there is less variation in movement of conductive pins 48a48c, both toward the outer surface of body 30 and inward, thereby reducing the occurrence of shorts between conductive pins 48a-48a and with contacts rings 38a-38c. Use of distal frame 36 also simplifies the mold tool by simplifying and reducing the exit holes required. Distal frame 36 also provides a simplified process for aligning and positioning the conductive pins 48a-48c within the mold cavity, which is otherwise a more time consuming and costly process when arranging the conductive pins through corresponding exit holes in the mold tool.

Also, by using a pre-molded distal frame 36 to arrange and locate the conductive pins 48a-48c and ring contacts 40 relative to one another and form connector assembly 78 (see FIG. 7) which can simply be loaded into the mold cavity, in lieu of the more complicated process or arranging and assembling the conductive pins and ring contacts within the mold cavity, molding cycle times can be shortened. Not only does this improve through-put of the process, a short cycle time also means that molding material (e.g., polymer material) will have less chance to degrade in the injection barrel of the molding press.

Additionally, distal frame 36 can easily be adapted and formed to have a desired distal geometry for any number of different lead connector configurations without requiring complex modifications/adaptations of the mold tool. As such, the use of distal frame 36 greatly simplifies the requirements of the injection molding tool, which would otherwise require separate molds or mold components for each different type of lead connector configurations.

Furthermore, the shafts in the distal frame through which lead connector elements are fed, such as shafts 66a-66c through which conductive pins 48a-48c extend, eliminate the flashing of mold material about such conductive pins that otherwise occurs about the conductive pins when being passed through exit holes in the mold tool. Thus, distal frame 36 also eliminates costly secondary processing that would otherwise be needed to remove such flash from the finished lead connector.

In short, as compared to conventional processes, employing a distal frame, according to embodiments described herein, better secures conductive wires/pins within the mold, simplifies the loading of lead connector components within the mold cavity, simplifies mold tooling requirements, simplifies/reduces secondary processing, and enables ready adaptation to provide desired distal geometry to any number of lead connector configuration without requiring substantial modifications to mold tooling.

Although specific embodiments have been illustrated and described herein, it will be appreciated by those of ordinary skill in the art that a variety of alternate and/or equivalent implementations may be substituted for the specific embodiments shown and described without departing from the scope of the present invention. This application is intended to cover any adaptations or variations of the specific embodiments discussed herein. Therefore, it is intended that this invention be limited only by the claims and the equivalents thereof.

What is claimed is:

1. A lead connector for an implantable medical device comprising:
    a cylindrical connector body having a proximal end and a distal end, a distal frame forming the distal end and a remainder of the connecter body comprising a mold material, a plurality of shafts extending through the distal frame from a rear face to a front face, the rear face abutting the mold material forming the remainder of the connector body;
    a plurality of ring contacts spaced apart along a length of the connector body between the proximal end and the distal end;
    a plurality of wires, each wire each wire having a proximal end coupled to an internal surface of a corresponding ring contact and extending through the mold material and through a corresponding one of the shafts and beyond the front face of the distal frame to a distal end of the wire, wherein mold material forming the remainder of the connector body extends partially into each shaft and about the corresponding conductive wire to form a plug;
    wherein a material of the distal frame is different from the mold material forming the remainder of the connector body.

2. The lead connector of claim 1, wherein an inner diameter of each shaft through the distal frame is larger than an outer diameter of the corresponding wire passing through the shaft.

3. The lead connector of claim 1, wherein mold material from forming the remainder of the connector body extends into each shaft, but does not extend to the front face of the distal frame, thereby eliminating any need for post processing.

4. The lead connector of claim 1, wherein the mold material forming the remainder of the connector body is configured to flow against the rear face of the distal frame thereby causing the distal frame to reflow at its rear face thereby forming a reflow interface coupling the distal frame and the remainder of the connector body.

5. The lead connector of claim 1, wherein the distal frame includes a plurality of lead-in structures extending from the rear face, one corresponding to each shaft, configured to receive and guide a corresponding wire into the corresponding shaft.

6. A distal frame for a lead connector positioned in a mold cavity, the distal frame comprising:
    a base having a front face, a rear face and an outer diameter, the base configured with a plurality of shafts extending between the front face and the rear face; and
    an extension extending from the front face of the base and configured with a central lumen extending through the extension;
    wherein the plurality of shafts receive a plurality of wires from the lead connector such that the wires extend through the rear face of the base and extend out beyond the front face of the base; and
    wherein the rear face of the base combined with the mold cavity define a cylindrical connector body of the lead connector when a mold material is injected into the mold cavity.

7. The distal frame of claim 6, wherein the connecter body comprises a mold material configured to flow against the rear face of the distal frame thereby causing the distal frame to reflow at its rear face thereby forming a reflow interface coupling the connector body and the distal frame.

8. The distal frame of claim 7, wherein a material of the distal frame is different from the mold material forming the remainder of the connector body.

9. The distal frame of claim 7, wherein a material of the distal frame is the same as the mold material forming the remainder of the connector body.

10. The distal frame of claim 6, wherein an inner diameter of each shaft through the distal frame is larger than an outer diameter of the corresponding wire passing through the shaft.

11. The distal frame of claim 6, wherein the outer diameter of the distal frame is configured to match an inside diameter of a mold cavity, such that during molding of the connector body the rear face of the base is configured to block the flow of mold material thereby preventing the mold material from reaching the front face of the base.

12. The distal frame of claim 6, further comprising at least one of tapered openings and lead-in structures at the through-holes on the rear face.

13. The distal frame of claim 6, wherein the geometry of the distal frame is different than the geometry of the mold cavity.

* * * * *